(12) United States Patent
Cui et al.

(10) Patent No.: US 12,197,832 B2
(45) Date of Patent: Jan. 14, 2025

(54) METHOD FOR DETERMINING DYNAMIC WETLAND BOUNDARY BASED ON HYDROLOGY, ORGANISM AND SOIL ELEMENTS

(71) Applicant: Beijing Normal University, Beijing (CN)

(72) Inventors: Baoshan Cui, Beijing (CN); Xuan Wang, Beijing (CN); Tian Xie, Beijing (CN); Yijia Fu, Beijing (CN); Yu Chen, Beijing (CN)

(*) Notice: Subject to any disclaimer, the term of this patent is extended or adjusted under 35 U.S.C. 154(b) by 246 days.

(21) Appl. No.: 17/946,325

(22) Filed: Sep. 16, 2022

(65) Prior Publication Data

US 2023/0090928 A1    Mar. 23, 2023

(30) Foreign Application Priority Data

Sep. 18, 2021    (CN) .......................... 202111101077.4

(51) Int. Cl.
*G06F 30/28*    (2020.01)
*G01N 33/24*    (2006.01)

(52) U.S. Cl.
CPC .......... *G06F 30/28* (2020.01); *G01N 33/246* (2013.01)

(58) Field of Classification Search
CPC .............................. G01N 33/246; G06F 30/28
See application file for complete search history.

(56) References Cited

FOREIGN PATENT DOCUMENTS

| CN | 110234150 A | * | 9/2019 | ........... H04B 17/309 |
| CN | 112986045 A | | 6/2021 | |

* cited by examiner

*Primary Examiner* — Bijan Mapar
(74) *Attorney, Agent, or Firm* — Addison D. Ault; IPGentleman Intellectual Property Services, LLC

(57) ABSTRACT

The invention discloses a method for determining dynamic wetland boundary based on hydrology, organism and soil elements, including the following steps: step 1: extracting dynamic wetland hydrology boundary; step 2: obtaining data on wetland vegetation; step 3: obtaining data on wetland soil; step 4: simulating dynamic wetland vegetation boundary and dynamic wetland soil boundary according to the data from step 1 to step 3; step 5: determining dynamic wetland boundary; the invention can reflect the dynamic wetland boundary in multiple dimensions comprehensively and accurately.

1 Claim, 5 Drawing Sheets

Farthest boundary

METHOD FOR DETERMINING DYNAMIC WETLAND BOUNDARY BASED ON HYDROLOGY, ORGANISM AND SOIL ELEMENTS

BACKGROUND OF THE INVENTION

1. Field of the Invention

The invention belongs to the wetland range definition method of disciplines such as ecology, biology and hydrology, in particular to a method for determining dynamic wetland boundary based on hydrology, organism and soil elements.

2. Description of Related Art

Wetland, known as the "kidney of the earth", has great ecological service functions such as flood storage, water purification, water conservation and climate regulation; as one of the most valuable ecosystems with the richest biodiversity and the highest productivity, wetland provides an important guarantee for human survival and development. However, under the influence of high-intensity human activities and climate change, ecological problems of wetland are prominent gradually. At present, it is an important research branch of ecology and also one of the hot issues related to disciplines such as biology and hydrology to explain the intrinsic mechanism of wetland, highlight the existing problems and threats of wetland, and put forward suggestions on wetland management and ecological restoration.

Wetland boundary is the most basic ecological characteristic of wetland, and defining wetland boundary is the basic information for knowing many structures and functions of wetland, such as vegetation distribution, ecological pattern, water and soil conservation capacity, habitat function and biodiversity. Determining wetland boundary is the first step to know a wetland; a wetland has multiple characteristics and complex multi-layers, wetland boundary has dynamic characteristics in different dimensions, and the wetland boundaries determined based on different elements are different, thus causing great difficulties and uncertainties to the determination of wetland boundary.

At present, the methods to determine wetland boundary at home and abroad mainly include identification method based on wetland flooding characteristics, identification method based on vegetation transition zone, technical method of wetland classification based on hydromorphology, and identification method based on remote sensing technology. However, these methods only involve one of aspects such as hydrology, soil and vegetation, and have some shortcomings such as parameter complexity and applicability insufficiency. Therefore, the invention designs a method for determining dynamic wetland boundary based on hydrology, organism and soil elements by considering "three elements of wetland" comprehensively, namely wetland hydrology, wetland vegetation and wetland soil, and identifying the dynamic change characteristics of wetland boundary; the invention can reflect the dynamic wetland boundary comprehensively and accurately.

SUMMARY OF THE INVENTION

The invention is to provide a method for determining dynamic wetland boundary based on hydrology, organism and soil elements, and the invention can reflect the dynamic wetland boundary in multiple dimensions comprehensively and accurately.

A method for determining dynamic wetland boundary based on hydrology, organism and soil elements includes the following steps:

step 1: extracting dynamic wetland hydrology boundary;
step 2: obtaining data on wetland vegetation;
step 3: obtaining data on wetland soil;
step 4: simulating dynamic wetland vegetation boundary and dynamic wetland soil boundary according to the data from step 1 to step 3;
step 5: determining dynamic wetland boundary.

In a preferred embodiment, the dynamic wetland hydrology boundary in step 1 includes two boundaries: actual water surface boundary, and animal and plant remain boundary.

In a preferred embodiment, the step 1 includes the following sub-steps:

sub-step 1: conducting on-site investigation by high-precision handheld GPS, or using remote sensing image with a resolution of less than 2 m, so as to obtain the actual water surface boundary; searching for the animal and plant remains through on-site investigation;

sub-step 2: tracking and recording the positions of animal and plant remains by high-precision handheld GPS, so as to obtain the animal and plant remain boundary, wherein the animal and plant remain boundary is the farthest hydrology boundary; overlaying the actual water surface boundary and the animal and plant remain boundary, so as to obtain the dynamic wetland hydrology boundary.

In a preferred embodiment, the step 2 includes the following sub-steps:

sub-step 1: laying investigation line transects in the direction perpendicular to the wetland hydrology boundary, with an interval of 100 m-500 m among the line transects, with the water surface boundary taken as the starting point of investigation line transect;

sub-step 2: setting three investigation quadrats (1 m×1 m) on the line transects every 10 m, recording the vegetation coverage, the plant species and the numbers and coverage of various plants in the quadrats, and determining the species of hygrophytes and xerophytes thereof;

sub-step 3: calculating the importance value of each species, wherein the importance value is the sum of relative coverage, relative density and relative frequency of each species; calculating the importance value proportion of hygrophyte.

In a preferred embodiment, the step 3 includes the following sub-steps:

sub-step 1: in the investigation quadrats, collecting the soil samples within the range of 0 cm-10 cm of the surface layer, weighing the soil samples, then drying them at 105° C., and finally calculating the soil moisture content by using the weight difference;

sub-step 2: taking the animal and plant remain boundary, i.e., the farthest hydrology boundary, as a benchmark, and calculating the minimum perpendicular distance of quadrat away from the actual water body boundary:

$$D = \left[(x_0 - x)^2 + (y_0 - y)^2\right]^{\frac{1}{2}}$$

$$D_m = \min_{(x,y) \in R} D$$

Where, $(x_0, y_0)$ and $(x, y)$ represent the decimal latitude and longitude coordinates of pixels of each quadrat and hydrology boundary respectively, R represents the decimal latitude and longitude coordinates set of all pixels of hydrology boundary, D represents the minimum perpendicular distance of quadrat away from the actual water body boundary, $D_m$ represents the quadrat with the minimum perpendicular distance away from the actual water body boundary and with the greatest influence by water body, and the smaller the index D, the closer the hydrological connectivity between the quadrat and the wetland water body;

sub-step 3: conducting regression analysis on the minimum perpendicular distance of quadrat away from the actual water body boundary, the hygrophyte proportion and the measured soil moisture content so as to obtain a regression equation, and simulating the wetland boundary by using the geographically weighted regression model in ArcGIS software so as to fit curves of the measured and estimated hygrophyte proportion or soil moisture content;

sub-step 4: verifying the simulation effect of the model: when the fitted curve $R^2$ is greater than or equal to 0.6, the simulation result of wetland boundary is reliable, so that the dynamic wetland vegetation boundary and dynamic wetland soil boundary are obtained; when the fitted curve $R^2$ is less than 0.6, it is necessary to readjust the model or conduct field investigation again;

sub-step 5: considering the wetland hydrology boundary, wetland vegetation boundary and wetland soil boundary comprehensively, and taking the actual water surface boundary as a benchmark, so as to analyze the differences of the three boundaries on the perpendicular line of each pixel of water surface boundary; taking the boundary point with the largest D among the three boundary points as the wetland boundary of this perpendicular line, so as to obtain the dynamic wetland boundary.

The method for determining dynamic wetland boundary based on hydrology, organism and soil elements has the following beneficial effects:

1. The invention provides a wetland boundary determination method based on geographically weighted regression, and the method is involved with hydrology, organism and soil elements, with less workload and lower requirements for time scale of data, and can reflect the range of wetland in different dimensions.
2. The invention, with high-accuracy simulation results, wide application scope and convenient and simple data acquisition, can show the dynamic evolution of wetland boundary clearly, intuitively and comprehensively, integrate the hydrology boundary, soil boundary and vegetation boundary and simulate the dynamic wetland boundary, so as to propose wetland management suggestions accordingly.

DETAILED DESCRIPTION OF THE PREFERRED EMBODIMENTS

The detailed embodiment of the invention will be described below in order to facilitate those skilled in the technical field to understand the invention. However, it should be clear that the invention is not limited to the scope of the detailed embodiment. For those skilled in the technical field, if various changes are within the spirit and scope of the invention defined and determined by the appended claims, and these changes are obvious, then all inventions and creations using the concepts of the invention are protected.

Figure 1:
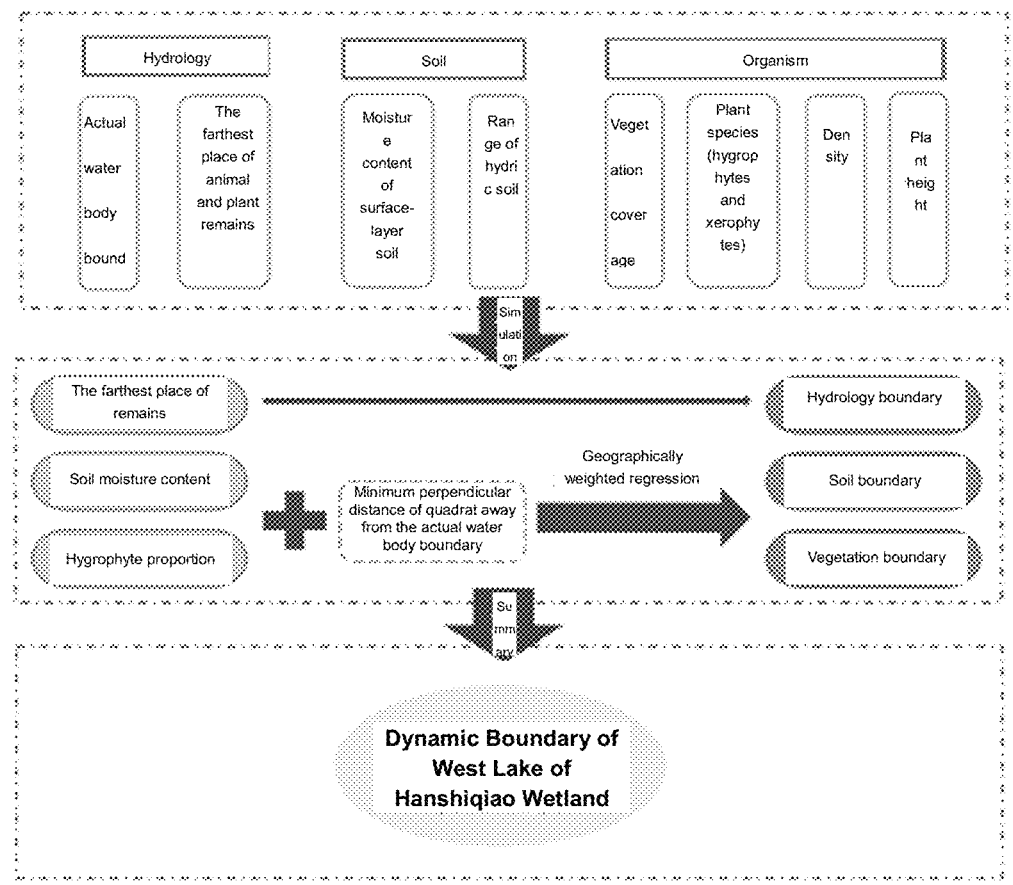
FIG. 1 is an operation flow chart of the invention.

Embodiment 1: Taking West Lake of Hanshiqiao Wetland, Shunyi District, Beijing as an Example to Determine Dynamic Wetland Boundary As shown in FIG. 1, the method for determining dynamic wetland boundary based on hydrology, organism and soil elements in the invention is carried out according to the following steps:

Step 1: Extracting Dynamic Wetland Hydrology Boundary

Figure 2:
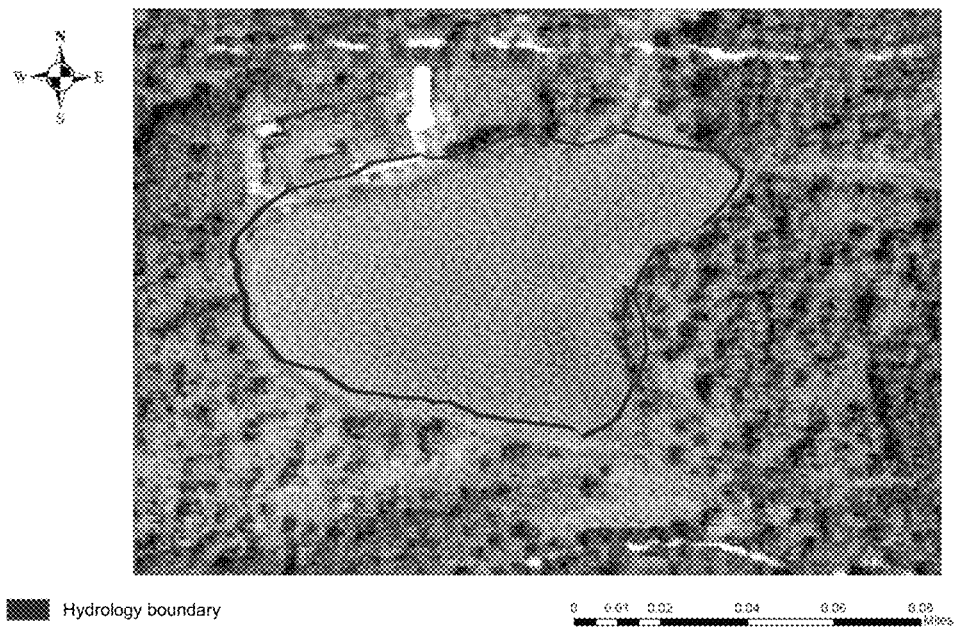
FIG. 2 is a hydrology boundary diagram in Embodiment 1.

As shown in FIG. 2, the dynamic wetland hydrology boundary in step 1 includes two boundaries: actual water surface boundary, and animal and plant remain boundary. The actual water surface boundary is obtained through on-site investigation by high-precision handheld GPS or through remote sensing image with a resolution of less than 2 m; the animal and plant remain boundary is obtained by searching for the animal and plant remains through on-site investigation and then tracking and recording by high-precision handheld GPS, wherein the animal and plant remain boundary is the farthest hydrology boundary. The dynamic wetland hydrology boundary is obtained by overlaying the actual water surface boundary and the animal and plant remain boundary;

Step 2: Obtaining Data on Wetland Vegetation

Investigation line transects are laid in the direction perpendicular to the wetland hydrology boundary, with an interval of 100 m-500 m among the line transects, and the water surface boundary is taken as the starting point of investigation line transect; three investigation quadrats (1 m×1 m) are set on the line transects every 10 m, the vegetation coverage, the plant species and the numbers and coverage of various plants in the quadrats are recorded, and the species of hygrophytes and xerophytes thereof are determined; the importance value of each species is calculated, wherein the importance value is the sum of the relative coverage, relative density and relative frequency of each species; the importance value proportion of hygrophyte is calculated;

Step 3: Obtaining Data on Wetland Soil

In the investigation quadrats, the soil samples within the range of 0 cm-10 cm of surface layer are collected, weighed and then dried at 105° C., and finally the soil moisture content is calculated by weight difference;

Step 4: Simulating Dynamic Wetland Vegetation Boundary and Dynamic Wetland Soil Boundary Taking the animal and plant remain boundary, i.e., the farthest hydrology boundary, as a benchmark, and calculating the minimum perpendicular distance of quadrat away from the actual water body boundary:

$$D = [(x_0 - x)^2 + (y_0 - y)^2]^{\frac{1}{2}}$$
$$D_m = \min_{(x,y) \in R} D$$

Figure 3:
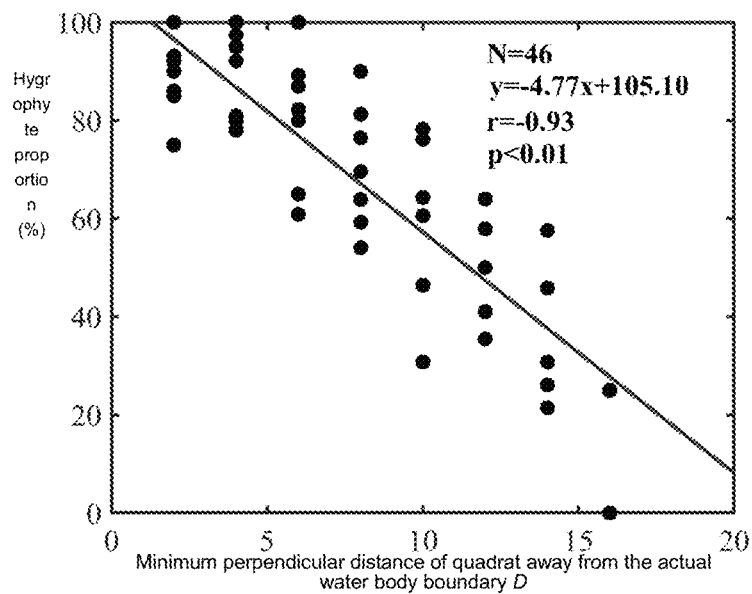
FIG. 3 is an analysis chart of vegetation data dependency in Embodiment 1.
Figure 4:
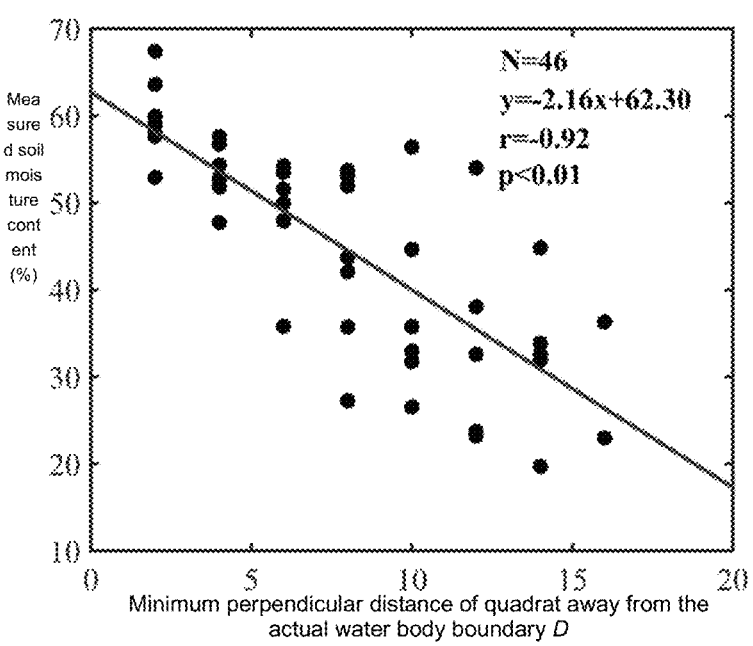
FIG. 4 is an analysis chart of soil data dependency in Embodiment 1.
Figure 5:
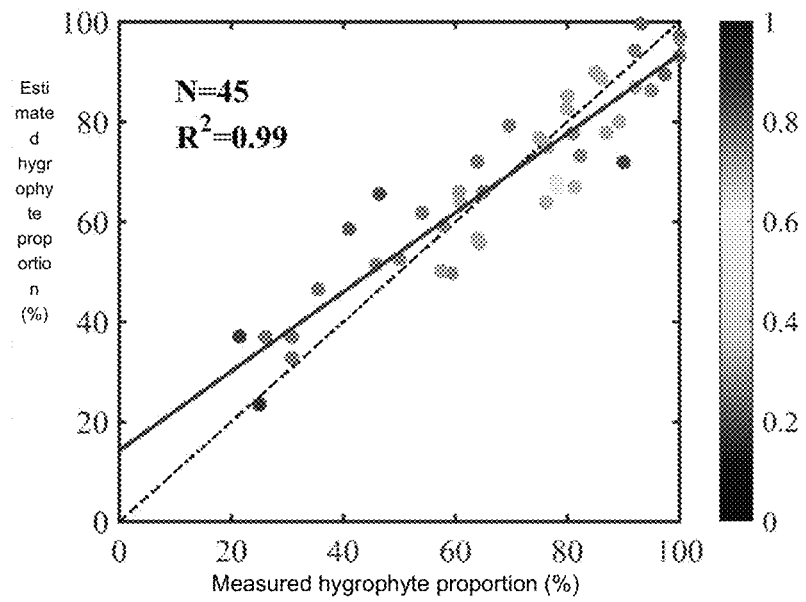
FIG. 5 is a scatter diagram of vegetation boundary verification results in Embodiment 1.
Figure 6:
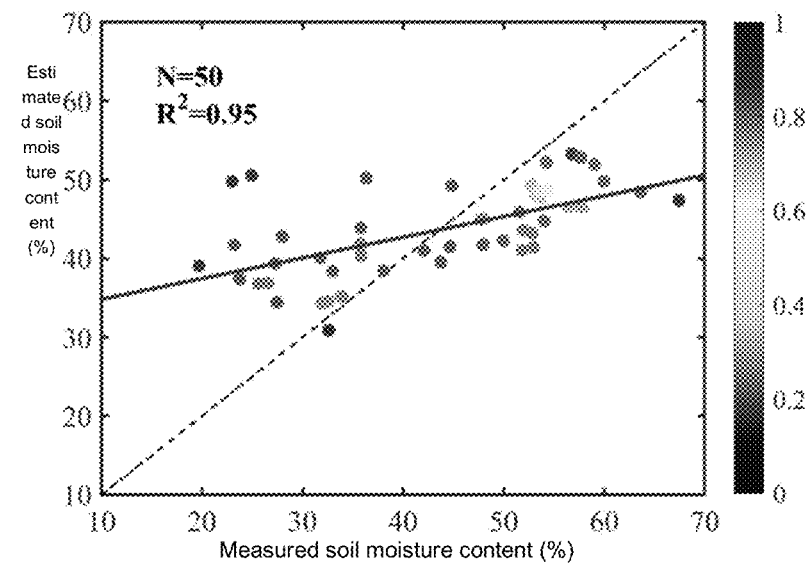
FIG. 6 is a scatter diagram of soil boundary verification results in Embodiment 1.
Figure 7:
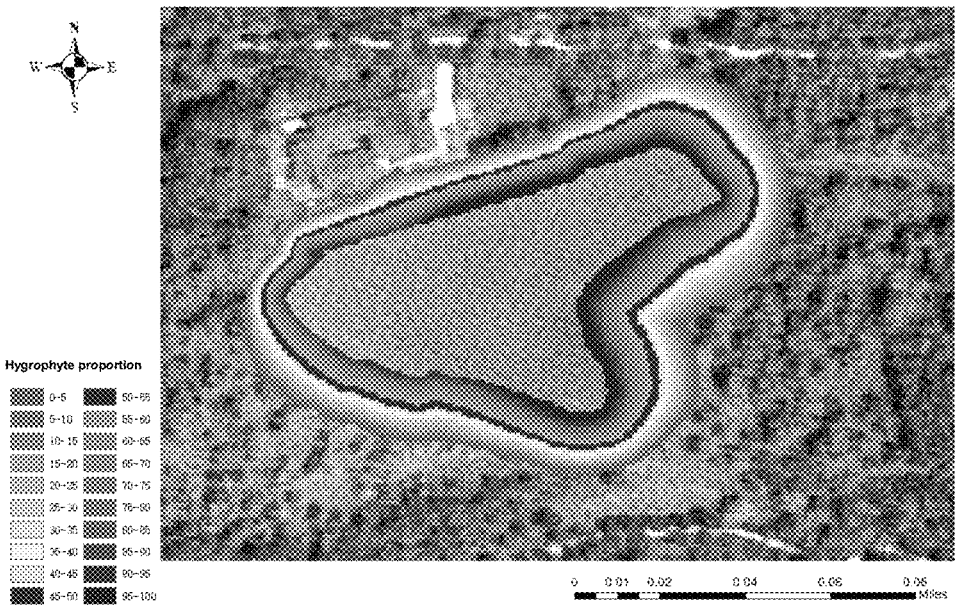
FIG. 7 is a vegetation boundary diagram in Embodiment 1.
Figure 8:
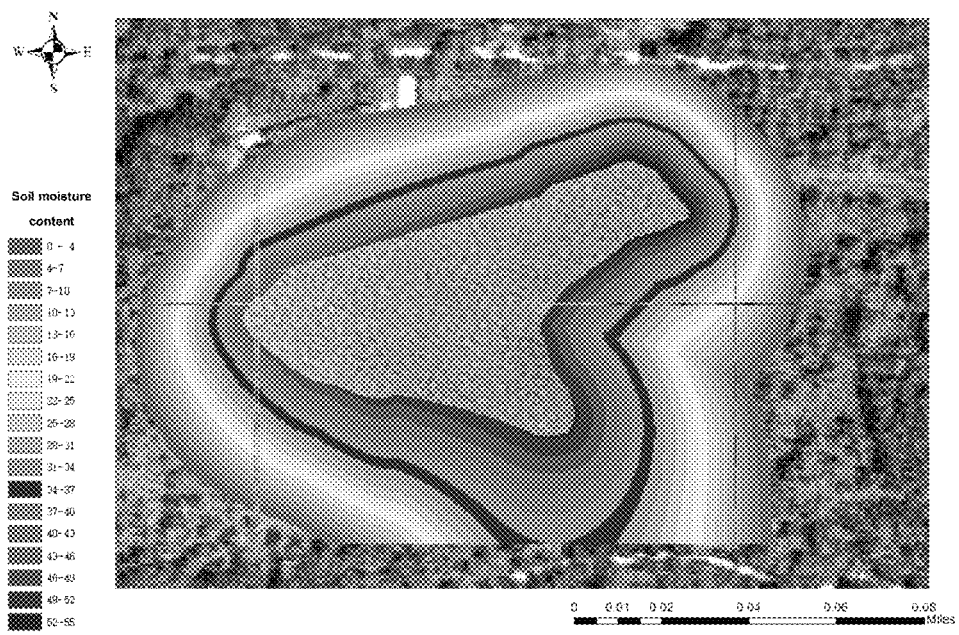
FIG. 8 is a soil boundary diagram in Embodiment 1.

Where, $(x_0, y_0)$ and $(x, y)$ represent the decimal latitude and longitude coordinates of pixels of each quadrat and hydrology boundary respectively, R represents the decimal latitude and longitude coordinates set of all pixels of hydrology boundary, D represents the minimum perpendicular distance of quadrat away from the actual water body boundary, $D_m$ represents the quadrat with the minimum perpendicular distance away from the actual water body boundary and with the greatest influence by water body, and the smaller the index D, the closer the hydrological connectivity between the quadrat and the wetland water body;

As shown in FIGS. 3 and 4, regression analysis is conducted on the minimum perpendicular distance of quadrat away from the actual water body boundary, the hygrophyte proportion and the measured soil moisture content, so as to obtain a regression equation;

Spatial statistics toolbox—spatial relationship modeling tool set—geographically weighted regression tool is selected in ArcGIS software, the wetland vegetation boundary or wetland soil boundary is simulated by geographically weighted regression model, curves of the measured and estimated hygrophyte proportion or soil moisture content are fitted, and the simulation effect of the model is verified. As shown in FIGS. 5 and 6, the fitted curve $R^2$ is greater than 0.6, this shows that the simulation result of wetland boundary is reliable; as shown in FIGS. 7 and 8, when the soil moisture content is 34%-37% or the hygrophyte proportion is 45%-55%, the soil boundary or vegetation boundary is obtained respectively;

Step 5: Determining Dynamic Wetland Boundary

Figure 9:
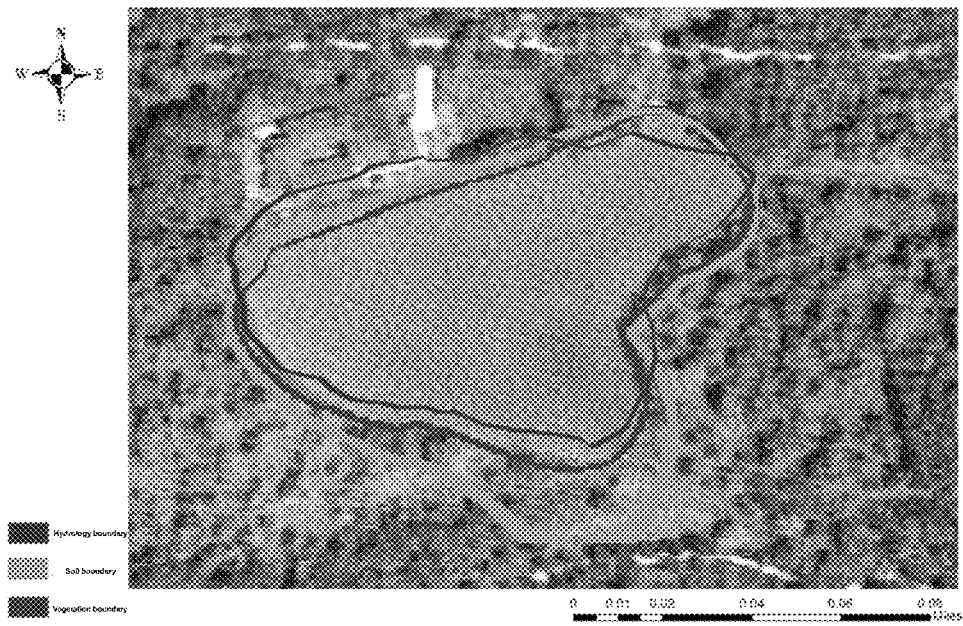
FIG. 9 is an overlay chart of hydrology boundary, vegetation boundary and soil boundary in Embodiment 1.
Figure 10:
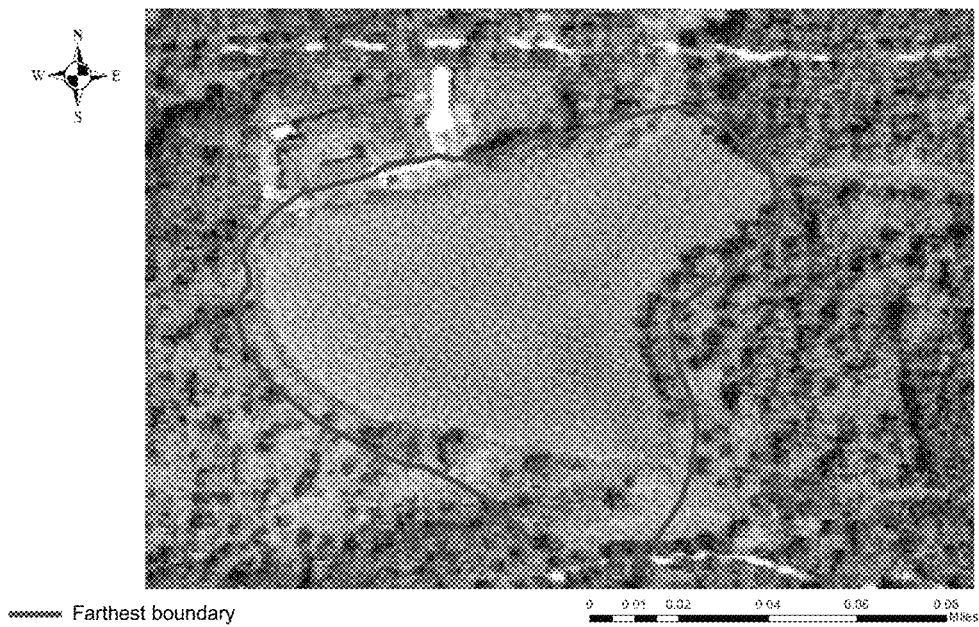
FIG. 10 is a dynamic wetland boundary diagram in Embodiment 1.

As shown in FIG. 9, considering the wetland hydrology boundary, wetland vegetation boundary and wetland soil boundary comprehensively, and taking the actual water surface boundary as a benchmark, so as to analyze the differences of the three boundaries on the perpendicular line of each pixel of water surface boundary; taking the boundary point with the largest D among the three boundary points as the wetland boundary of this perpendicular line, so as to obtain the dynamic wetland boundary, as shown in FIG. 10.

What is claimed is:

1. A method, implemented on a GPS unit and a computer system comprising a processor, geographical image analysis software, and a non-transitory memory unit, for determining dynamic wetland boundary based on hydrology, organism and soil elements, wherein the method comprises the following steps step 1: extracting a dynamic wetland hydrology boundary
step 2: obtaining data on wetland vegetation
step 3: obtaining data on wetland soil
step 4: simulating a dynamic wetland vegetation boundary and a dynamic wetland soil boundary according to the data from step 1 to step 3; and
step 5: determining the dynamic wetland boundary;
wherein the dynamic wetland hydrology boundary in step 1 comprises two boundaries: an actual water surface boundary, and an animal and plant remain boundary
wherein the step 1 comprises the following sub-steps:
sub-step 1: conducting on-site investigation by high-precision handheld GPS, or using remote sensing image with a resolution of less than 2 m, so as to obtain the actual water surface boundary; searching for the animal and plant remains through on-site investigation; and
sub-step 2: tracking and recording the positions of animal and plant remains by high-precision handheld GPS, so as to obtain the animal and plant remain boundary, wherein the animal and plant remain boundary is a farthest hydrology boundary; overlaying the actual water surface boundary and the animal and plant remain boundary, so as to obtain the dynamic wetland hydrology boundary;
wherein the step 2 comprises the following sub-steps:
sub-step 1: laying investigation line transects in a direction perpendicular to the wetland hydrology boundary, with an interval of 100 m-500 m among the line transects, with the water surface boundary taken as a starting point of investigation line transect;
sub-step 2: setting three investigation quadrats (1 m×1 m) on the line transects every 10 m, recording vegetation coverage, plant species and numbers and coverage of various plants in the quadrats, and determining species of hygrophytes and xerophytes thereof; and
sub-step 3: utilizing said computer comprising a processor, geographic image analysis software, and a non-transitory memory unit, calculating an importance value of each species, wherein the importance value is a sum of relative coverage, relative density and relative frequency of each species; calculating an importance value proportion of hygrophyte;
wherein the step 3 comprises the following sub-steps
sub-step 1: in the investigation quadrats, collecting soil samples within a range of 0 cm-10 cm of the surface layer, weighing the soil samples, then drying them at 105° C., and finally calculating the soil moisture content by using a weight difference;
sub-step 2: taking the animal and plant remain boundary, i.e., the farthest hydrology boundary, as a benchmark, and calculating a minimum perpendicular distance of quadrat away from the actual water body boundary $$D = [(x_0 - x)^2 + (y_0 - y)^2]^{\frac{1}{2}}$$
$$D_m = \min_{(x,y) \in R} D$$

where, $(x_0, y_0)$ and $(x, y)$ represent decimal latitude and longitude coordinates of pixels of each quadrat and hydrology boundary respectively, R represents a decimal latitude and longitude coordinates set of all pixels of hydrology boundary, D represents the minimum perpendicular distance of quadrat away from the actual water body boundary, $D_m$ represents the quadrat with the minimum perpendicular distance away from the actual water body boundary and with greatest influence by water body, and the smaller the index D, the closer the hydrological connectivity between the quadrat and the wetland water body;

sub-step 3: utilizing said computer comprising a processor, geographic image analysis software, and a non-transitory memory unit, conducting regression analysis on the minimum perpendicular distance of quadrat away from the actual water body boundary, a hygrophyte proportion and the measured soil moisture content so as to obtain a regression equation, and simulating the wetland boundary by using the geographically weighted regression model in geographic image analysis software so as to fit curves of the measured and estimated hygrophyte proportion or soil moisture content;

sub-step 4: verifying the simulation effect of the model: when the fitted curve $R^2$ is greater than or equal to 0.6, a simulation result of the wetland boundary is reliable, so that the dynamic wetland vegetation boundary and dynamic wetland soil boundary are obtained; when the fitted curve $R^2$ is less than 0.6, it is necessary to readjust the model or conduct field investigation again; and sub-step 5: considering the wetland hydrology boundary, wetland vegetation boundary and wetland soil boundary comprehensively, and taking the actual water surface boundary as a benchmark, so as to analyze differences of the three boundaries on the perpendicular line of each pixel of water surface boundary.

* * * * *